United States Patent
Baek et al.

(10) Patent No.: US 9,597,625 B1
(45) Date of Patent: Mar. 21, 2017

(54) METHOD OF MANUFACTRING AN ANTIBACTERIAL FILTER COMPRISING COPPER-BASED COMPOUND PARTICLES

(71) Applicant: BS SUPPORT CO., LTD., Suwon-si (KR)

(72) Inventors: Seung Woo Baek, Anyang-si (KR); Mun Sun Kim, Ansan-si (KR)

(73) Assignee: BS SUPPORT CO., LTD., Suwon-si (KR)

( * ) Notice: Subject to any disclaimer, the term of this patent is extended or adjusted under 35 U.S.C. 154(b) by 0 days.

(21) Appl. No.: 15/349,426

(22) Filed: Nov. 11, 2016

Related U.S. Application Data

(63) Continuation-in-part of application No. 15/218,395, filed on Jul. 25, 2016, which is a continuation-in-part of application No. PCT/KR2014/003630, filed on Apr. 25, 2014.

(30) Foreign Application Priority Data

Feb. 6, 2014 (KR) ........................ 10-2014-0013372

(51) Int. Cl.
| | |
|---|---|
| *B01D 39/14* | (2006.01) |
| *B01D 46/00* | (2006.01) |
| *A61L 9/16* | (2006.01) |
| *A61L 2/238* | (2006.01) |
| *A61L 2/232* | (2006.01) |
| *B01D 39/16* | (2006.01) |

(52) U.S. Cl.
CPC .......... *B01D 46/0028* (2013.01); *A61L 2/232* (2013.01); *A61L 2/238* (2013.01); *A61L 9/16* (2013.01); *B01D 39/1676* (2013.01); *A61L 2209/14* (2013.01); *B01D 2239/045* (2013.01); *B01D 2239/0442* (2013.01); *B01D 2239/0464* (2013.01); *B01D 2239/0478* (2013.01); *B01D 2275/30* (2013.01)

(58) Field of Classification Search
CPC combination set(s) only.
See application file for complete search history.

(56) References Cited

U.S. PATENT DOCUMENTS

| | | | |
|---|---|---|---|
| 4,906,462 | A | 3/1990 | Miki et al. |
| 4,916,108 | A | 4/1990 | McLaughlin et al. |
| 5,071,622 | A | 12/1991 | Dunson, Jr. |
| 8,197,695 | B2 | 6/2012 | Cousins et al. |

FOREIGN PATENT DOCUMENTS

| | | |
|---|---|---|
| JP | 02126856 | 5/1990 |
| KR | 100843191 | 7/2008 |
| KR | 101189677 | 10/2012 |
| KR | 101591118 | 2/2016 |
| WO | 2013096284 | 6/2013 |

OTHER PUBLICATIONS

International Search Report—PCT/KR2014/003630 dated Nov. 6, 2014.

*Primary Examiner* — Duane Smith
*Assistant Examiner* — Adam W Bergfelder
(74) *Attorney, Agent, or Firm* — Cantor Colburn LLP

(57) ABSTRACT

Provided is a method of manufacturing an antibacterial filter including copper-based compound particles. The method comprises the steps of preparing a porous medium containing minute pores allowing a fluid to pass therethrough and coating copper sulfide particles on inner surfaces of the minute pores of the porous medium. The sulfur compound particles have a chemical structure of $Cu_xS_y$ (wherein x/y=0.8 to 1.5).

6 Claims, 4 Drawing Sheets

METHOD OF MANUFACTRING AN ANTIBACTERIAL FILTER COMPRISING COPPER-BASED COMPOUND PARTICLES

CROSS-REFERENCE TO RELATED APPLICATION

This application is a continuation of U.S. Ser. No. 15/218,395, filed on Jul. 25, 2016, which is a continuation in part of PCT Application No. PCT/KR2014/003630 filed on Apr. 25, 2014, which claims priority to and the benefit of Korean Application No. 10-2014-0013372 filed on Feb. 6, 2014, in the Korean Patent Office, the entire contents of which are incorporated herein by reference.

BACKGROUND OF THE INVENTION

The present invention relates to an antibacterial filter including a copper-based compound, and more particularly to an antibacterial filter including a copper-based compound that uses a copper-based compound having electrical conductivity to improve antibacterial and deodorizing activities.

A filter, as a means for removing noxious substances from a fluid, is a device for separating contaminants through pores by way of porosity. There are various types of filters in accordance with their intended use, including ceramic filters, polymer filters, etc. The indoor air contains different microorganisms, such as bacteria, fungi, viruses, or the like. Such microorganisms floating in the air cause airborne infection or environmental diseases and thus act injuriously on the health. The microorganisms contained in the indoor air can be primarily removed through air filters used to eliminate dust. But, the microorganisms, having a tenacious hold on life, proliferate on the surface of the filter to produce biologically generated volatile organic compounds harmful to the human body or reenter the room.

To solve the above-mentioned problem, there has recently been suggested a technique for preventing proliferation of microorganisms with an application of inorganic antibacterial preparations, e.g., silver, copper, gold, $TiO_2$, etc. or an organic antibacterial preparation, e.g., catherchine, chitosan, phytoncide, Hosta capitata Nakai extract, shrubby sophora extract, ginko biloba leaf extract, herb extract, pine tree leaf extract, maple leaf extract, etc., on the surface of a filter. For example, Korea Patent No. 843191 discloses a filter containing nanoparticles. Silver is excessively expensive despite its high antibacterial effect and ease of use. Like silver, sulfur is known to possess high antibacterial activity. But, the application of sulfur into practical use is much limited, because sulfur has unsolved problems of toxic properties and difficulty of processing.

BRIEF SUMMARY OF THE INVENTION

It is an object of the present invention to provide an antibacterial filter including a copper-based compound that is relatively inexpensive, easy to process, non-toxic and excellent in antibacterial and deodorizing activities.

To achieve the object of the present invention, there is provided an antibacterial filter including a copper-based compound that comprises: a porous medium containing minute pores available for a fluid to pass through; and copper sulfide applied on the surface of the porous medium by coating or dispersed in the porous medium, the sulfur compound having a chemical structure of $Cu_xM_y$ (where M is any one selected from Group 15 to 17 elements of the periodic table; and x/y=0.8 to 1.5).

In the antibacterial filter of the present invention, M is any one selected from the group consisting of S, F and Cl. Preferably, the sulfur compound is copper sulfide. Further, the porous medium comprises any one selected from the group consisting of ceramic, a metal and a polymer. Preferably, the porous medium comprises a polymer. Furthermore, the porosity of porous medium is 10 to 40%, and the porous medium is prepared using a supercritical fluid. In this regard, the antibacterial filter has an antibacterial activity of $1\times10^4$ counts/ml to $1\times10^6$ counts/ml, and a deodorizing activity of 90 to 98%.

EFFECTS OF INVENTION

According to the antibacterial filter including a copper-based compound of the present invention, the use of a sulfur compound contributes to making the antibacterial filter at a relatively low cost with ease of processing and non-toxicity. Further, the sulfur compound including copper sulfide is excellent in antibacterial and deodorizing activities, and its application makes it possible to improve the antibacterial and deodorizing activities of the antibacterial filter.

BRIEF DESCRIPTION OF THE SEVERAL VIEW OF THE DRAWING

DETAILED DESCRIPTION OF THE INVENTION

Figure 1:
FIG. 1 is a photograph showing copper sulfide particles applied in the present invention.

Hereinafter, the preferred embodiments of the present invention will be described in detail with reference to the accompanying drawings. It is to be understood, however, that the present invention may be embodied in various forms not to be interpreted as limiting. The embodiments of the present invention are provided for those skilled in the art to understand the present invention more completely.

In the embodiments of the present invention, a sulfur compound including copper sulfide is used to provide an antibacterial filter that is relatively inexpensive, easy to process, non-toxic, and excellent in antibacterial and deodorizing activities. For this, a description will be given as to an antibacterial filter using a sulfur compound dispersed in or applied to a porous medium and, more specifically, to its antibacterial and deodorizing activities. On the other hand, the antibacterial filter of the present invention may be manufactured by applying a coating of the sulfur compound on the surface of a porous medium through deposition or dyeing or mixing particles of the sulfur compound with the porous medium.

The antibacterial filter of the present invention not only does the antibacterial activity to eliminate toxic microorganisms through the holes in the porous medium, but also the deodorizing activity to remove a foul odor. The material for the porous medium may be a polymer, a ceramic, or a metal, preferably a polymer. Specific examples of the polymer include polyurethane resin, nylon resin, etc.; those of the ceramic may include zeolite, silica, alumina, zirconium phosphate, etc.; and those of the metal include aluminum, etc. The porous medium contains minute pores, through which a fluid passes. The pore size or the porosity of the porous medium may vary depending on the environment in which the antibacterial filter of the present invention is used. In the embodiment of the present invention, a porous medium comprised of a polymer is given as a preferred example. But, the porous medium may be comprised of a ceramic or a metal within the scope of the present invention.

A chemical foaming agent, liquid nitrogen, or a supercritical fluid may be incorporated into the porous medium to form pores. More specifically, while extruded at a temperature higher than the melting temperature by 30 to 40° C., a polymer resin used as a matrix for the porous medium is mixed with a chemical foaming agent, liquid nitrogen, or supercritical carbon dioxide that is side-fed. As the polymer resin is extruded, the evaporated foaming agent, nitrogen or carbon dioxide is released into the air to form pores.

The copper-based compound applied to the embodiment of the present invention is preferably copper sulfide (CuS). Copper sulfide is prepared by reacting copper sulfate ($CuSO_4$) with a salt selected from sulfides, fluorides, and chlorides in an aqueous phase at mole ratio of 1:1 at 10 to 80° C. In this regard, the synthesis is performed under the condition that the synthesized particle of copper sulfide has a chemical structure of $Cu_xS_y$ (where x/y is 0.8 to 1.5). Specific examples of the sulfides available in the present invention may include sodium sulfide, iron sulfide, potassium sulfide, zinc sulfide, etc.; specific examples of the fluorides available in the present invention may include sodium fluoride, iron fluoride, potassium fluoride, zinc fluoride, etc.; and specific examples of the chlorides available in the present invention may include sodium chloride, iron chloride, potassium chloride, zinc chloride, etc. In this case, the copper sulfide synthesized from sodium sulfide and copper sulfate is most excellent in the antibacterial activity.

When the reaction temperature is less than 10° C. in the synthesis of copper-based particles, the reactivity of copper sulfate and the salt decreases to deteriorate the deodorizing activity despite the good antibacterial activity. When the reaction temperature exceeds 80° C., the reaction rate is extremely high so as to increase the density of the crystals on the surface of copper sulfide and the concentration of copper, resulting in good deodorizing activity and poor antibacterial activity. Further, the ratio x/y of the copper-based particles less than 0.8 leads to excessively high concentration of sulfur (S), consequently with good antibacterial activity and poor deodorizing activity. The ratio x/y of the copper-based particles greater than 1.5 contributes to an increase in the concentration of copper (Cu), which improves the deodorizing activity and deteriorates the antibacterial activity.

Hereinafter, a description will be given as to the process for manufacturing an antibacterial filter in two methods: applying a coating of copper sulfide as a sulfur compound to a porous medium; or dispersing copper sulfide particles in a porous medium.

<Antibacterial Filter with Copper Sulfide Coating>

The method for applying a coating of copper sulfide to a porous medium according to an embodiment of the present invention involves stirring a predetermined amount of copper sulfide in a solvent such as isopropyl alcohol (IPA) at the room temperature for several hours to prepare a coating solution with good dispersability. Then, the coating solution is applied to the porous medium by dip coating. The coated porous medium is dried for several hours to scores of hours and then subjected to an annealing process at $T_c$ to $T_m$ for scores of minutes. In order to obtain a filter with good antibacterial and deodorizing activities, the procedures are repeatedly performed in the same manner as described above to form a coating of copper sulfide at high concentration on the surface of the porous medium.

<Antibacterial Filter with Dispersed Copper Sulfide Particles>

A porous medium of copper sulfide may have pores made by using a foaming agent or adding liquid nitrogen or a supercritical fluid. More specifically, while extruded at a temperature higher than the melting temperature of the resin by about 30 to 40° C., the polymer resin used as a matrix for the porous medium and copper sulfide are mixed sufficiently with a chemical foaming agent, liquid nitrogen, or supercritical carbon dioxide that is side-fed. As the polymer resin mixed with copper sulfide is extruded, a filter comprising a porous medium of copper sulfide with pores is completed. The porosity of the filter is suitably 10 to 40%, more preferably 20 to 30%. When the porosity is less than 10%, the contact area is too small to display a good deodorizing activity. When the porosity is greater than 40%, it is hard to get a filter form. The porosity may be controlled by the weight ratio of the resin to the foaming agent, the temperature, the rotating speed of the screw, the retention time, the L/D ratio (where L is the length of the compounder screw; and D is the diameter of the screw), etc.

When a chemical foaming agent is used, it has a lower evaporation temperature than the thermoplastic resin used as a matrix and thus kept in the gas state while moved by the screw. During the extrusion, the chemical foaming agent is released into the air to form pores. In the case of using liquid nitrogen or a supercritical fluid, which is supplied under high pressure, it is designed to maintain high pressure in the extrusion step. In other words, the liquid nitrogen or supercritical fluid supplied by side feeding is sufficiently mixed with the resin and then extruded. In the extrusion step, the evaporated nitrogen and carbon dioxide are released into the air to form pores. The chemical foaming agent is in wide use, because it is relatively inexpensive and requires a simple facility. But, the use of the chemical foaming agent possibly causes a pyrolysis of the resin and makes it hard to control the fine pores uniform. The liquid nitrogen or supercritical carbon dioxide costs high but advantageously enables it to make minute pores uniform.

Figure 2:
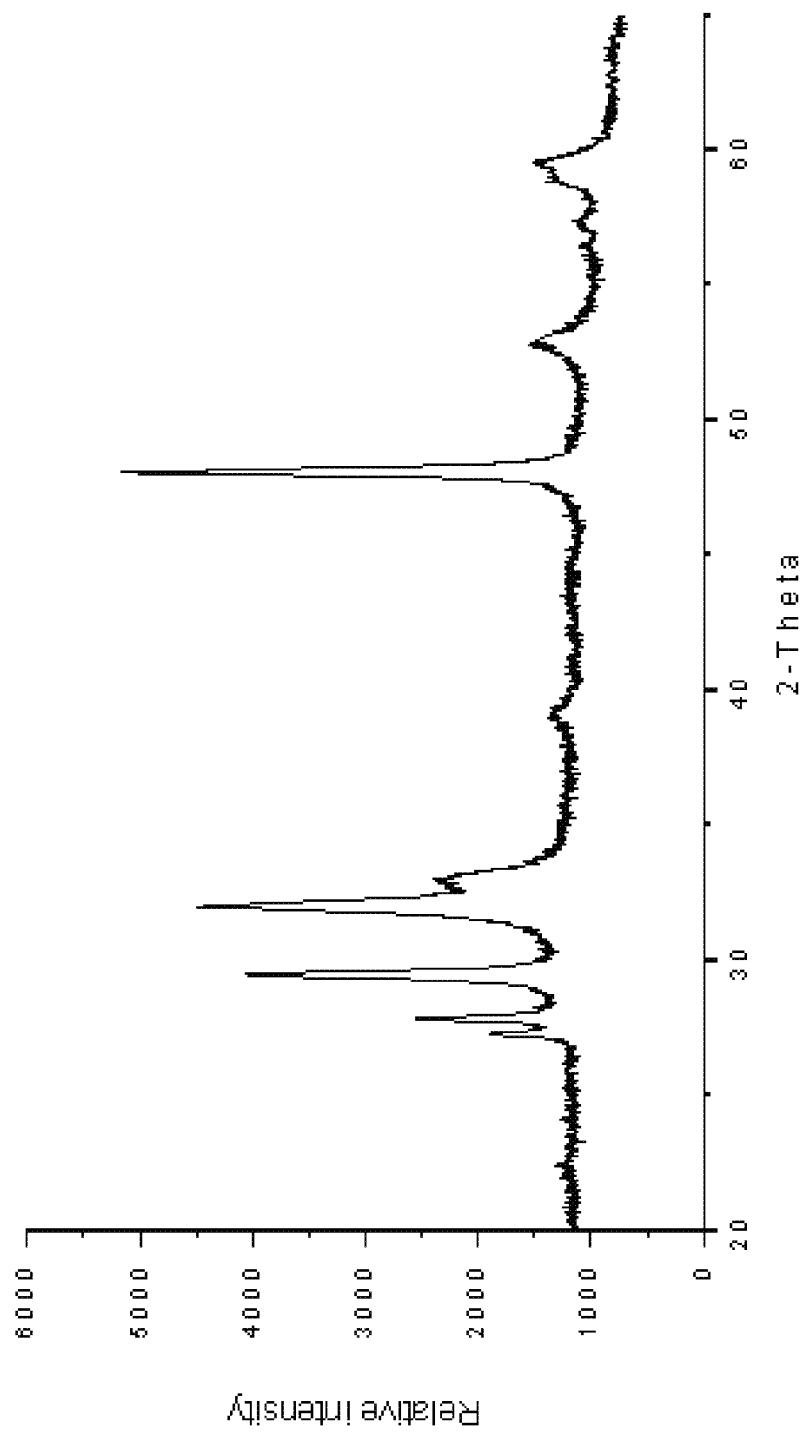
FIG. 2 is an XRD graph showing the crystalline structure of copper sulfide applied in the present invention.
Figure 3:
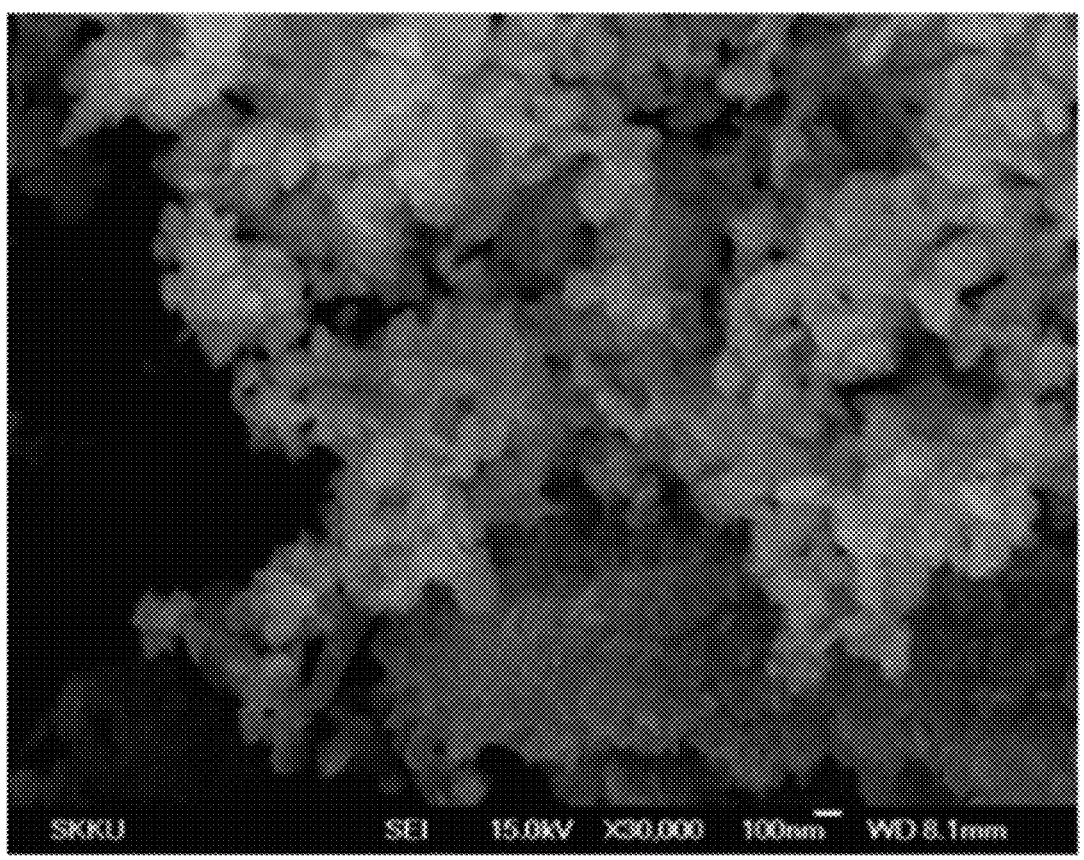
FIG. 3 is a 30,000× microscopic image showing the copper sulfide applied in the present invention.
Figure 4:
FIG. 4 is a photograph showing the porous antibacterial filter prepared using a chemical foaming agent and copper sulfide according to the present invention.

An exemplary method for manufacturing the antibacterial filter of the present invention is given as follows. $CuSO_4$ and $Na_2S$ in an amount of one mole each are added to distilled water and stirred to prepare an aqueous solution, which is then put into an isothermal reactor at 50° C. to synthesize copper sulfide (CuS) as shown in FIG. 1. In this regard, the x/y ratio is 1.02. The copper sulfide thus obtained has the crystalline structure peculiar to copper sulfide as shown in FIG. 2, and its particle image magnified by a factor of 30,000 is presented in FIG. 3. Referring to FIG. 3, there appears no peak for the sulfur, which does not have a crystalline structure, whereas peaks for the copper appear at 55, 65, 99, 125, and 137 degrees. The copper sulfide thus prepared is mixed with the nylon resin to form an antibacterial filter as shown in FIG. 4.

The activity evaluation of the antibacterial filter prepared in the embodiment of the present invention is performed in the manner as follows.

(1) Average Particle Diameter

The average particle diameter of the copper sulfide and metal particles is measured with a particle size analyzer (ELS-Z2, Otsuka Electronics Co., Japan).

(2) Antibacterial Activity

A culture medium with *Escherichia Coli* (ATCC 25922) is put in contact with a specimen and incubated at 25° C. for 24 hours. After incubation, the bacterial growth is determined to evaluate the antibacterial effect of the specimen.

(3) Deodorizing Activity 1 g of the copper-based particles is put into a reactor and then 10,000 ng/ml of gaseous formaldehyde is injected. After 5 minutes, the concentration of the formaldehyde eliminated is determined to evaluate the deodorizing effect of the copper-based particles. The concentration of the remaining gaseous formaldehyde is determined with a gas chromatograph (Agilent 6890, Aglient Technologies Inc., U.S.A).

(4) Copper/Sulfur Component

The copper-to-sulfur molar ratio of the copper sulfide particles is determined with an inductively coupled plasma mass spectrometer (Agilent 7500, Aglient Technologies Inc., U.S.A.).

(5) Porosity

The porosity (%) ($=[(D_i-D_p)/D_i]\times 100$, where $D_i$ is the density of the filter without pores; and $D_p$ is the density of the filter with pores) of the porous filter is determined by measuring the density of the specimen. The density measurement is performed with an electronic scale (XP204V, Mettler-Toledo Co., Swiss).

The copper sulfide used in the antibacterial filter according to the embodiment of the present invention has the antibacterial activity of $1\times 10^4$ counts/ml to $1\times 10^6$ counts/ml, and the deodorizing activity of 90 to 98%. Further, the copper/sulfur ratio, i.e., x/y ratio is 0.8 to 1.5, and the porosity is suitably 10 to 40%, more preferably 20 to 30% Accordingly, the antibacterial filter of the present invention makes the use of the properties of copper sulfide to secure the antibacterial and deodorizing effects required to antibacterial filters. Furthermore, copper sulfide is relatively inexpensive, easy to process, and non-toxic, so the antibacterial filter using copper sulfide is considered to be more useful than the conventional antibacterial filters using silver.

Although the preferred embodiments of the present invention have been described in detail, it is understood that the present invention should not be limited to these exemplary embodiments but various alternatives can be made by those skilled in the art within the spirit and scope of the present invention as hereinafter claimed.

What is claimed is:

1. A method of manufacturing an antibacterial filter including copper-based compound particles, comprising the steps of:
    preparing a porous medium containing minute pores allowing a fluid to pass therethrough; and
    coating copper sulfide particles on inner surfaces of the minute pores of the porous medium,
    wherein the sulfur compound particles have a chemical structure of $Cu_xS_y$ (wherein x/y=0.8 to 1.5).

2. The method in claim 1, wherein the copper sulfide particles are formed by synthesizing a copper sulfide (CuS) and a copper sulfate ($CuSO_4$) in a molar ratio of 1:1.

3. The method in claim 2, wherein the copper sulfide (CuS) and the copper sulfate ($CuSO_4$) are synthesized in an aqueous solution of 10 to 80° C.

4. The method in claim 1, wherein the porous medium has a porosity of 10 to 40%.

5. The method in claim 1, wherein the porous medium is prepared using a supercritical fluid.

6. The method in claim 1, wherein the antibacterial filter has an antibacterial activity of $1\times 10^4$ counts/ml to $1\times 10^6$ counts/ml.

* * * * *